United States Patent [19]

Mitsumaki et al.

[11] Patent Number: 5,677,188
[45] Date of Patent: Oct. 14, 1997

[54] ANALYZING METHOD AND APPARATUS FOR LIQUID SAMPLE

[75] Inventors: Hiroshi Mitsumaki, Mito; Katsuaki Takahashi, Katsuta, both of Japan

[73] Assignee: Hitachi, Ltd., Tokyo, Japan

[21] Appl. No.: 414,056

[22] Filed: Mar. 30, 1995

Related U.S. Application Data

[63] Continuation of Ser. No. 796,629, Nov. 22, 1991, abandoned.

[30] Foreign Application Priority Data

Nov. 28, 1990 [JP] Japan ................................ 2-322851

[51] Int. Cl.$^6$ ............................................... G01N 35/02
[52] U.S. Cl. .................. 436/47; 436/43; 436/55; 422/64; 422/68.1; 422/67; 422/82.05; 364/497; 364/500
[58] Field of Search ................ 422/62, 64, 65, 422/66, 67, 50, 68.1; 436/43, 50, 47, 49, 55; 364/497, 500

[56] References Cited

U.S. PATENT DOCUMENTS

| Re. 34,012 | 7/1992 | Azuma et al. | 422/64 |
|---|---|---|---|
| 4,158,545 | 6/1979 | Yamashita et al. | 436/50 |
| 4,315,891 | 2/1982 | Sakurada | 422/64 |
| 4,451,433 | 5/1984 | Yamashita et al. | 422/63 |
| 4,612,289 | 9/1986 | Furuta | 422/64 |
| 4,678,752 | 7/1987 | Thorne et al. | 435/291 |
| 4,805,469 | 2/1989 | Commarmot | 422/64 |
| 4,919,887 | 4/1990 | Wakatake | 436/43 |
| 5,049,359 | 9/1991 | Azuma et al. | 422/67 |

FOREIGN PATENT DOCUMENTS

| 355823 | 2/1990 | European Pat. Off. . |
|---|---|---|
| 409126 | 1/1991 | European Pat. Off. . |
| 2528182 | 12/1983 | France . |
| 57-69254 | 4/1982 | Japan . |
| 60-11167 | 1/1985 | Japan . |

OTHER PUBLICATIONS

Patent Abstracts of Japan, Abstract of Japanese Patent Publication No. 63-52063, Publication Date Jul. 26, 1988, vol. 012266.

IBM Technical Disclosure Bulletin, "Overlapped Processing in Wet Chemical Analyzer", vol. 19, No. 3, Aug. 1976, pp. 1022-1024.

*Primary Examiner*—Christopher Kim
*Attorney, Agent, or Firm*—Fay, Sharpe, Beall, Fagan, Minnich & McKee

[57] ABSTRACT

An analyzing method and apparatus for a liquid sample are determines in which the value of density or activity for an analysis item is through optical measurement of a reaction solution of a liquid sample and a reagent. When an instruction of measurement for a plurality of analysis items about each sample on a sample disk is inputted, a controller selects for each sample an analysis item in which a time duration from the start of a reaction until the final optical measurement point is the longest, and allots the selected analysis item to a loading reaction vessel while allotting the remaining analysis items to the succeeding reaction vessels in a sequence from an item having a longer time duration. A sample supplying device and a reagent supplying device make necessary operations on the basis of the sequence of arrangement of the analysis items in which the minimum time is obtained, and a reaction solution is optically measured by a fixed photometer. Thereby, the overall analytical processing time can be shortened.

10 Claims, 4 Drawing Sheets

FIG.2

| | | | | CHEMISTRY PARAMETERS | | | |
|---|---|---|---|---|---|---|---|
| TEST | [ ALP ] | 04-01 | | | | | |
| ASSAY CODE | [ RATE-A ] | | [ 10 ] | [ ] | WAVELENGTH(SUB/MAIN) | [ 505 ]/[ 450 ] | |
| ASSAY POINT | [ 17 ]-[ 30 ]-[ 0 ]-[ 0 ] | | | DILUTION | [ 123 ] [ 99 ] | | |
| | | < CLASS 1 > | | < CLASS 2 > | | | |
| S.VOL. (NORMAL) | [ 5.0 ] | [ 10.0 ] [ 100 ] | [ 5.0 ] [ 10.0 ] [ 100 ] | | | | |
| S.VOL. (DECREASE) | [ 3.0 ] | [ 0.0 ] [ 0 ] | [ 5.0 ] [ 10.0 ] [ 100 ] | | | | |
| S.VOL. (INCREASE) | [ 6.0 ] | [ 0.0 ] [ 0 ] | [ 5.0 ] [ 10.0 ] [ 100 ] | | | | |
| ABS. LIMIT | [ 20000 ] | | [ 20000 ] | [ INCREASE ] | | | |
| PROZONE LIMIT | [ 0 ] | | [ 0 ] | [ UPPER ] | | | |
| REAGENT R1 | [ 100 ] [ 200 ] [ 123 ] [ 30 ] | | | | | | |
| R2 | [ 50 ] [ 50 ] [ 100 ] [ 20 ] | | | | | | |
| R3 | [ 200 ] [ 60 ] [ 111 ] [ 10 ] | | | | | | |
| R4 | [ 150 ] [ 100 ] [ 222 ] [ 30 ] | | | | | | |
| CALIB. TYPE | [ LINEAR ] | [ 1 ] [ 2 ] [ 0 ] | | | | | |
| AUTO CALIB. | | | | | | | |
| TIME OUT R.B | [ 100 ] | | SD LIMIT | [ 999.9 ] | | | |
| SPAN | [ 100 ] | | DUPLICATE LIMIT | [ 32000 ] | | | |
| 2 POINT | [ 50 ] | | SENSITIVITY LIMIT | [ 0 ] | | | |
| FULL | [ 20 ] | | S\ABS LIMIT | [-32000 ][ 32000 ] | | | |
| CHANGE LOT | [ FULL ] | | COMPENSATED LIMIT | [ ] | | | |
| BOTTLE | [ 2 POINT ] | | | | | | |

△ MEASUREMENT OF CELL BLANK

▲ ADDITION OF SAMPLE/REAGENT (START OF REACTION)

○ FINAL OPTICAL MEASUREMENT POINT (COMPLETION OF REACTION)

● DATA PROCESSING ary reaction line to the main reaction line.

ANALYZING METHOD AND APPARATUS FOR LIQUID SAMPLE

This is a continuation application of Ser. No. 07/796,629, filed Nov. 22, 1991 abandoned.

BACKGROUND OF THE INVENTION

1. Field of the Invention

The present invention relates to an analyzing method and apparatus for a liquid sample, and more particularly to an analyzing method and apparatus in which the progression of a reaction of a sample is made in reaction vessels to measure a plurality of analysis items.

2. Description of the Prior Art

As for vital samples such as blood or urine, analytical measurements concerning a plurality of analysis items are made for each object or sample to be analyzed. One automatic analyzer for making such multi-item analysis is disclosed by, for example, U.S. Pat. No. 4,451,433.

In the analyzer disclosed by the U.S. Pat. No. 4,451,433, a sample and reagents adapted to a plurality of analysis items are successively pipetted into reaction vessels on a reaction line formed on a turntable and then subjected to reactions corresponding to individual analysis items. While rotating the turntable so that the array of reaction vessels passes through an optical measurement position of an absorptiometric photometer, the progression of a reaction of the sample is observed to measure the absorbance of each reaction solution, thereby determining the value of density or activity for each analysis item. A reaction vessel, for which the measurement has been completed, is cleaned on the reaction line and is used for a new sample.

The analyzer of the U.S. Pat. No. 4,451,433 is constructed such that all of the circularly arranged reaction vessels pass through an optical path of the photometer during a period of time required for the array of reaction vessels rotate by a distance equal to one rotation plus one vessel. With this construction, direct optical measurement for reaction solutions in all the reaction vessels becomes possible.

In such a kind of analyzer, the timing of a data processing for performing an operation for the determination of the value of density or activity is made equally for either analysis item in compliance with the system period of the analyzer.

In the case where a liquid sample is subjected to a chemical reaction or immunoreaction, analysis items requested for each object or sample to be analyzed involve a variety of reaction times (or times required until the completion of reaction) which extend from a shorter reaction time to longer reaction times, depending on the analysis items. In the analyzer disclosed by the U.S. Pat No. 4,451, 433, however, an analyzing time until the completion of a data processing for an analysis item having a shorter reaction time must be conformed equally to that for an analysis item having a longer reaction time. Therefore, time is wastefully consumed in regard to analysis items having short reaction time.

For such circumstances, some efforts are made to further improve the processing ability of an automatic analyzer when multi-item analysis is made. Such prior art includes JP-A-60-11167 and JP-A-57-69254.

JP-A-60-11167 discloses an analyzer in which a plurality of auxiliary reaction lines are provided along a main reaction line. A reaction vessel corresponding to an analysis item having a short reaction time is transported on only the main reaction line until it reaches measurement means. On the other hand, each of the reaction vessels corresponding to analysis items having longer reaction items is subjected to sample and reagent pipetting on the main reaction line, is thereafter transferred from the main reaction line onto an auxiliary reaction line so that it resides thereon for a predetermined time until a desired state of reaction is obtained, and is returned again to the main reaction line for transportation to the measurement means.

Also, JP-A-57-69254 discloses an analyzer in which a carrier block adapted to reciprocate on a reaction line and having a sample pipetting nozzle and a reagent pipetting nozzle mounted thereon is provided along the array of reaction vessels sent intermittently in a fixed direction, and the carrier block is moved so that the positions of sample addition from the sample pipetting nozzle and reagent addition from the reagent pipetting nozzle into reaction vessels on the reaction line are changed in accordance with analysis items and a suction nozzle for bringing a reaction solution to an analyzing section is inserted into a reaction vessel which arrives at a predetermined position.

In the method according to JP-A-60-11167, since reaction vessels corresponding to analysis items other than an analysis item having the shortest reaction time must be transferred one by one from the main reaction line to the auxiliary reaction lines and each of the transferred reaction vessels must be returned to the main reaction line after residence thereof on the auxiliary reaction line for a predetermined time, a complex mechanism for taking-in and taking-out of the reaction vessels is required. Further, a problem exists as to how to make a receiving space on the main reaction line when the reaction vessel is returned from the auxili Also, in the method according to JP-A-57-69254, since a mechanism for transporting the carrier block must be provided on the reaction line, the structure becomes complex. Further, the change of the sample adding or pipetting position on the reaction line in accordance with each analysis item requires the locating of each reaction vessel for sample reception to the pipetting position. In connection with this, a problem exists as to how to realize the supplying or positioning of such sample receiving reaction vessels.

SUMMARY OF THE INVENTION

An object of the present invention is to provide an analyzing method and apparatus in which a processing time for a sample to be analyzed for a plurality of analysis items can be shortened without complicating the structure of the apparatus.

According to one concept of the present invention, an analysis item, for which a processing time until the final optical measurement point of time is substantially the longest, is selected from among a plurality of analysis items designated for a sample, and the sample is added into reaction vessels on a reaction line with the selected analysis item being designated to become the first to be analyzed.

According to another concept of the present invention, the sequence of sample addition for a plurality of analysis items designated for a sample is determined on the basis of a period of time from the start of a reaction until the final optical measurement point of time for each analysis item so that a time from the start of a processing operation for that sample until the completion of optical measurements for all of the designated analysis items is shortened, and the sample is successively added into reaction vessels corresponding to the analysis items in accordance with the determined sequence of sample addition.

A time from the start of a processing or the start of a reaction for a sample on a reaction line until the acquisition of optical measurement data ultimately required for the determination of the value of density or activity differs depending on each analysis item. This time is termed a processing time for each analysis item. Also, a point of time, when the final measurement data used for an operation to yield the result for that analysis item are acquired, is termed the final optical measurement point of time. In the case in which a rate assay is to be made, as when the enzyme activity is determined, an optical measurement used for an operation is made plural times for the corresponding reaction solution during a period of time until the final optical measurement point of time is reached. In the case where an end point assay is to be made in connection with an analysis item having a longer reaction time, only one or two optical measurements are used for an operation, even tough the corresponding reaction solution passes through an optical measurement position plural times. When an operation for the determination of the value of density or activity is to be performed, data are usually taken plural times for one optical measurement to determine an average value. In the case where the optical measurement is made only one time, it becomes the final optical measurement.

In a usual analyzer of a discrete type, reaction vessels are arranged in order on a reaction line and the stop/movement of the reaction vessel array is repeated.

If a plurality of possible analysis items are designated for each object or sample and they are stored in a storage section of a controller or computer of the analyzer, the analyzer, when the final optical measurement point of time corresponding to each analysis item is inputted from an input device, can recognize the final optical measurement points of time for all the analysis items for each object. Since it is possible to know a processing time necessary for each analysis item on the basis of such data, the computer of the analyzer can select an analysis item having substantially the longest processing time among the plurality of processing times to store the selected analysis item into the storage section as the first of a sample supply sequence.

Also, considering a processing time for each analysis item for each object to be analyzed, the computer can determine the performance sequence for the sample supplying operations for the respective analysis items to minimize the overall processing time for that object. In the simplest way, the sample supplying operation is performed in a sequence from an analysis item having a longer processing time toward an analysis item having a shorter processing time. The determined sample supply sequence is registered into the storage section. The computer causes a sample supplying or adding device and a reagent supplying or adding device to operate on the basis of the registered sequence while allotting reaction vessels on a reaction line to analysis items so that the analysis items are arranged on the reaction line in accordance with the registered sequence.

The computer, which is the controller, functions as the sequence determining means for determining the sequence of arrangement of analysis items for the array of reaction vessels. A group of analysis items is then formed, for each sample, in the reaction vessel array. When considering only one group, the controller allots a reaction vessel at the top of that group (i.e., the highest priority) to an analysis item which has the longest processing time. Next, the remaining reaction vessels in that group arranged in the rear are allotted to analysis items having the processing times which become gradually shorter in accordance with the order of arrangement of those vessels in the reaction vessel array. Two or more analysis items having the same processing times are allotted to adjacent reaction vessels.

In a preferred embodiment of the present invention, each time an aliquot portion of a sample is supplied to a reaction line, an array of reaction vessels is transported so that the reaction vessels in the array cross a fixed optical measurement position. Accordingly, a reaction solution in each reaction vessel necessarily crosses the optical measurement position plural times. Therefore, it becomes possible to freely select the timing at which that reaction solution should be optically measured.

There may frequently appear the case where the final optical measurement for an analysis item having a short processing time is completed earlier than the final optical measurement for an analysis item which has a long processing time and in which a reaction was started preceding that in the former analysis item. In such a case, an operation for the determination of the value of density or activity for each analysis item is performed immediately at the point of time when the final optical measurement for that analysis item has been completed. Therefore, the sequence of performance of density or activity determining operations does not coincide with the sequence of arrangement of analysis items in a reaction vessel array. In other words, an operation for an analysis item, for which the final optical measurement is completed early, is performed without waiting for the final optical measurement for the preceding analysis item which has a longer processing time. Therefore, the timing of completion of operations for all analysis items is hastened as a whole, thereby shortening the time until the outputting of the results of measurement of the plurality of analysis items for each sample is completed.

On the other hand, as for the sample supplying operation performed for the reaction vessel on the reaction line, an analysis item having a short processing time takes the precedence of the other analysis items so as to have an earlier point of time for the start of a reaction than those of the other analysis items, thereby reducing a temporal influence on the other analysis items. A reaction for an analysis item having a shorter processing time is started in a reaction vessel which is sent to a predetermined sample supply or adding position later than a reaction vessel corresponding to an analysis item having a longer processing time. However, this contributes to the shortening of the overall processing time for the sample or object to be analyzed.

With the above construction, the sample supplying operation for each analysis item can be performed from the same sample supplying or adding position in the order of arrangement of reaction vessels on a reaction line, With the result that the overall processing time is shortened. Accordingly, an analyzing operation can be performed smoothly with no need of the provision of a mechanism for moving a reaction vessel on the reaction line to another place or a mechanism for moving a sample pipetting nozzle on the reaction line.

BRIEF DESCRIPTION OF THE DRAWINGS

FIG. 2 is a diagram showing one example of an measuring condition setting table which is displayed on a display screen in an embodiment of the present invention;

DESCRIPTION OF THE PREFERRED EMBODIMENTS

Embodiments of the present invention will now be explained referring to the accompanying drawings.

Figure 3:
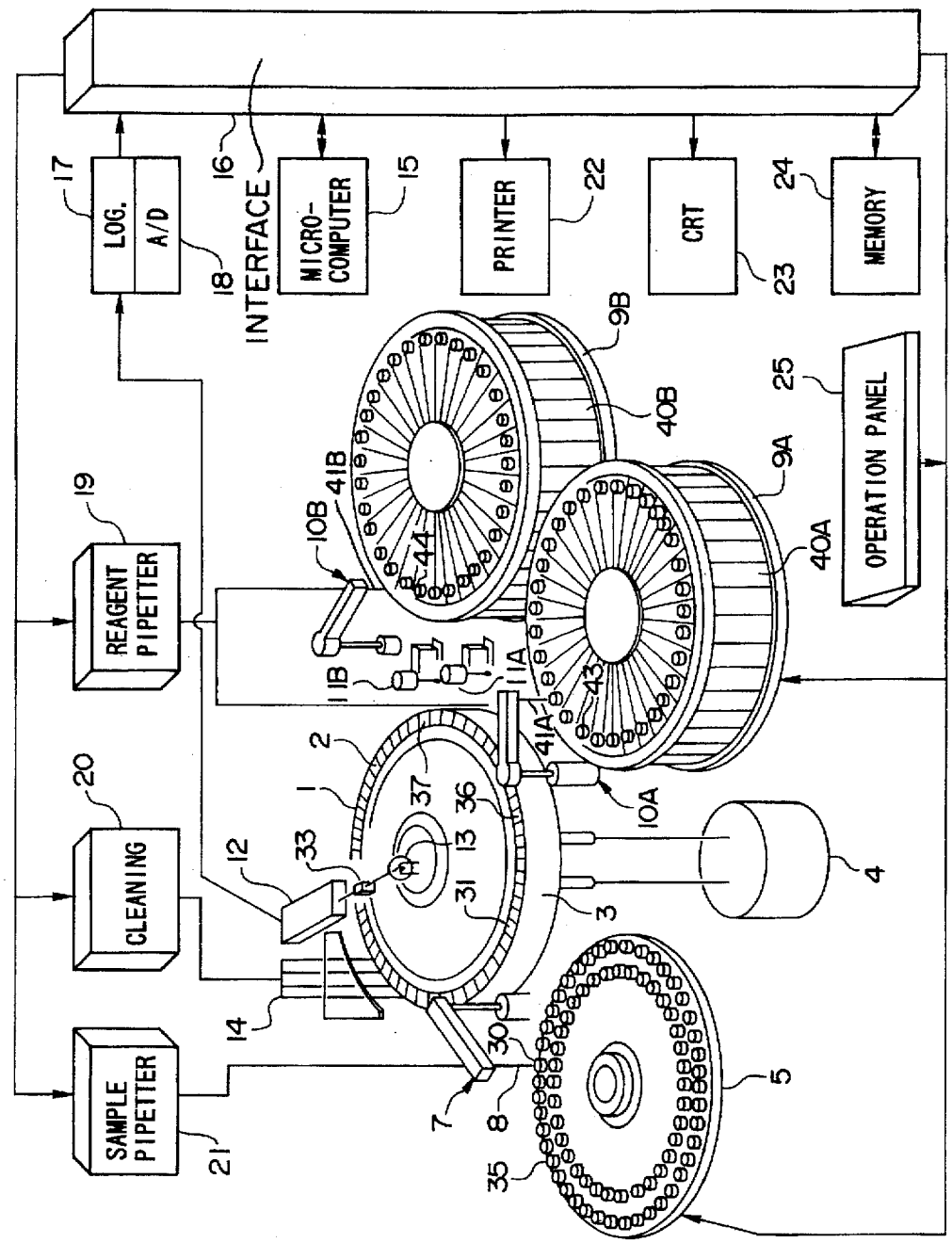
FIG. 3 shows in perspective view and in block diagram the construction of an automatic analyzer for realizing an embodiment of the present invention.

FIG. 3 shows the schematic construction of an automatic blood analyzer to which the present invention is applied. In FIG. 3, a reaction disk 1 is rotated and stopped by a known driving mechanism. One hundred twenty (120) reaction vessels 2 are arranged along the circumference of the reaction disk 1 to form a circular reaction line. The array of reaction vessels 2 is maintained at a constant temperature by a heat insulating bath 3. A heat-maintained liquid is supplied from a heat-maintained liquid supplying device 4 to the heat insulating bath 3. A sample adding position 31, two reagent adding positions 36 and 37, two agitating positions, an optical measurement position 33, cleaning positions, etc. are arranged at fixed points on the reaction line.

A sample disk 5 is rotated by a known driving mechanism. The driving mechanism can drive the sample disk 5 so that any one of a multiplicity of circumferentially arranged sample cups 35 is stopped at a fixed sample suction position 30. On the sample disk 5 are held a multiplicity of sample cups for a blood sample to be analyzed as well as sample cups for a standard sample and a control blood serum. A sample pipetting 21 provided with a suction/discharge pump is connected to a sample pipetting nozzle 8 which is held by a vertically and rotationally movable sample pipetting mechanism 7. The nozzle 8 sucks a part of a sample from the sample cup 35 placed at the sample suction position 30 on the sample disk 5 and holds it. The nozzle 8 is then rotated to the reaction disk 1 and discharges the volume of the held sample corresponding to the desired analysis item into the reaction vessel 2 which is stopped at the sample adding position 31.

A reagent supplying device includes first and second reagent disks 9A and 9B having a multiplicity of reagent reservoirs 40A and 40B for reserving reagents to cause reactions peculiar to the respective analysis items, mechanisms 10A and 10B for moving reagent pipetting nozzles 41A and 41B vertically and rotationally, and a reagent pipetter 19 having pumps for causing suction/discharge operations of the nozzles 41A and 41B independently.

The reagent supplying device is controlled in operation by a computer (or microcomputer) 15 and can add, at most, four kinds of reagents to the reaction vessel in connection with one analysis item. First and second reagents are selected from the first reagent disk 9A while second and third reagents are selected from the second reagent disk 9B. The selected reagent reservoirs 40A and 40B are located to predetermined reagent suction positions 43 and 44 through the rotation of the reagent disks 9A and 9B, and necessary reagents are pipetted or added from the reagent reservoirs into the reaction vessel 2 by the nozzles 41A and 41B. Reagent-added solutions in the reaction vessels are agitated by agitators 11A and 11B, respectively.

A multi-wavelength photometer 12 is disposed such that a light flux crosses the reaction line. White light from light source 13 is led to a spectroscope or dispersion section of the multi-wavelength photometer 12 through the optical measurement position 33 fixed on the reaction line, and a multiplicity of dispersed or separated light components of different wavelengths are simultaneously received by a photodetector such as a photodiode array. Only necessary ones of detected signals are logarithmically converted by a logarithmic converter 17 and are then converted by an A/D converter 18 into digital signals which are in turn used for an operation for determining the value of density or activity for an analysis item. The microcomputer 15 can operate on measurement data to output the result to a printer 22 and a CRT 23. Further, the microcomputer 15 can operate the various mechanisms or mechanical parts in the analyzer through an interface 16 in accordance with a desired program, can process analyzing or measuring conditions and various information inputted from an operation panel 25 and can store the processed information and data into its own storage section or an external memory 24 such as a floppy disk.

When an aliquot portion of the sample from a sample cup 35 is added by the sample pipetting nozzle 8 into a reaction vessel 2 which is temporarily stopped at the sample adding position 31 on the reaction disk 1, reagent solutions corresponding to analysis items are added into reaction vessels 2 which are stopped at the predetermined reagent adding positions 36 and 37. Thereafter, the reaction disk 1 is rotated by a distance equal to one rotation plus one vessel so that a reaction vessel next or adjacent to the above-mentioned reaction vessel is stopped at the sample adding position 31.

During this rotation operation, the photometer 12 makes optical measurements for all of the reaction vessels which pass through the optical measurement position 33. Such a rotation operation is made each time the sample is pipetted or added into a new reaction vessel. Accordingly, paying attention to one reaction vessel on the reaction line, the optical measurement for that reaction vessel by the photometer becomes possible at every rotation during a period of time after that reaction vessel starts from the sample adding position 31 and until it is stopped at a position past the optical measurement position 33 with the progression on the reaction line through the repetition of rotation and stop.

In the analyzer shown in FIG. 3, the number of times of optical measurement made for each reaction vessel on the reaction line during progression from the sample adding position 31 to the optical measurement position 33 until stopping there is set to be 100. In other words, there are involved 100 optical measurement points. In this case, the number of optical measurement points is proportional to the lapse of time.

The reagent adding position is set such that a time from the addition of a sample into a specified reaction vessel until the addition of a first reagent thereto is shorter than 3 minutes. Among analysis items requiring a fewer number of reagents, there may be an analysis item for which the addition of only one reagent suffices and which has a short reaction time. In that case, available measurement data ultimately used for an operation for determination of the value of density or activity for the analysis item can be acquired at an early time after the sample addition. As for an analysis item having a short reaction time, in the analyzer shown in FIG. 3, an optical measurement point of time after 3 minutes from the sample addition can be set as the final optical measurement point for that analysis item. The final optical measurement point for each analysis item can be selected from among optical measurement points of, for example, 3, 5, 10, 15, 20 and 30 minutes. Other optical measurement points may be set by changing the contents of the memory.

In the analyzer shown in FIG. 3, a cleaning operation using a cleaning solution or liquid is performed for a reaction vessel at a temporary stop position which is past the optical measurement position 33. A cleaner 14 includes a plurality of solution suction/exhaust nozzles and a plurality of cleaning solution discharge (or delivery) nozzles for exhausting the used reaction solution from the reaction vessel and for cleaning the reaction vessel. A cleaning pump system 20 serves to supply the cleaning solution to the cleaner 14 and to exhaust the solution from the cleaner 14. Even during the cleaning operation, the rotation/stop of the reaction disk 1 is made at the period of 20 seconds. In this analyzer, optical measurement is made in a state in which an ion exchange water lastly added to the reaction vessel in the cleaning step remains in the reaction vessel, and the result of measurement is used for a data processing operation as a cell blank measured value for the next stage.

When a sample processing operation by the analyzer shown in FIG. 3 is to be performed, measuring conditions concerning several tens of items capable of being measured by the analyzer are inputted beforehand. Though there are a variety of analysis items which may become the objects of analysis, only seven analysis items are shown in Table 1 by way of example.

TABLE 1

| Symbol | ITEM NAME | PRINCIPLE OF MEASUREMENT | FINAL OPTICAL MEASUREMENT TIME (MINUTE) |
| --- | --- | --- | --- |
| A | TRIGLYCERIDE | ENZYME METHOD | 10 |
| B | GLUCOSE | HEXOKINASE METHOD | 8 |
| C | CREATININE | JAFFE METHOD | 4 |
| D | AMYLASE | G-5 SUBSTRATE METHOD | 5 |
| E | CHOLESTEROL | ENZYME METHOD | 10 |
| F | ALBUMIN | BCG METHOD | 10 |
| G | CALCIUM | OCPC METHOD | 3 |

When measuring conditions concerning analysis items are to be set, parameter setting tables are fetched onto a display screen of the CRT 23 and item-by-item the conditions are inputted from the operation panel 25. FIG. 2 shows one example of display screen for setting the measuring condition and corresponds to the case where a test item is alkaline phosphates (ALP). At least an analysis item name, an optical measurement point and the timing of a data processing operation based on measurement data are displayed on the display screen with a correspondence to an analysis item.

A column A in TEST in FIG. 2 is a column into which an analysis item name is to be inputted. The analysis item name is displayed in the column A by positioning a cursor at the column A and inputting "ALP" from the operation panel 25. This analysis item can be registered into a storage section of a controller or the microcomputer 15 by depressing an acknowledge key on the operation panel 25 after the inputting. A column T in ASSAY CODE in FIG. 2 is an operation timing input column which indicates how many minutes from the start of a reaction between a sample and a reagent should be allowed before performing an operation for determining the value of activity or density. A column at the left of the column T is a column that indicates either a rate assay or an end point assay. By positioning the cursor at the column T and inputting "10" from the operation panel 25 the value is displayed in the column T. If the acknowledge key on the operation panel 25 is depressed after the inputting, the operation timing of 10 minutes can be registered into the storage section of the microcomputer 15.

A series of columns M in ASSAY POINT in FIG. 2 are input columns which indicate what optical measurement points numbered from the start of a reaction concerning the corresponding analysis item should be used for an operation on acquired measurement data. In the case of a usual end point assay, only one optical measurement point is inputted. In the case of a rate assay, however, an application or use start measurement point and an application end measurement point corresponding to (or indicative of) a time zone used for operation on acquired measurement data can be inputted. In the example of ALP shown in FIG. 2, "17" and "30" are inputted in the series of columns M. Namely, it is indicated that optical measurement data acquired between the 17th optical measurement point and the 30th optical measurement point should be used for operation. Thereby, it is possible to determine the rate of change in absorbance for a reaction in a desired time zone. In the shown example, the 30th optical measurement becomes the final optical measurement.

Columns belonging to S. VOL. in FIG. 2 are columns used for setting, the volumes of a sample to be added, and columns belonging to "REAGENT" columns used for setting the volumes of reagents to be added and the volumes of an extruding liquid.

By depressing the acknowledge key on the operation panel 25 after all necessary measuring conditions have been inputted onto the setting screen, the contents of designated data are registered into the storage section such as a random access memory (RAM) in the microcomputer 15. Subsequently, if a setting table for the next analysis item is fetched onto the display screen of the CRT 23 and measuring conditions are similarly set, designated data are registered into the memory. Once such setting of measuring conditions is made, data can be used for some time as is. In a routine opperation, therefore, the condition setting operation does not make the burden heavy for an operator.

In the routine operation, an analysis operation is started after objects or samples to be analyzed have been set on a sampler or the sample disk 5 of the automatic analyzer. The operation of the analyzer will now be explained referring to FIGS. 1 and 3.

Figure 1:
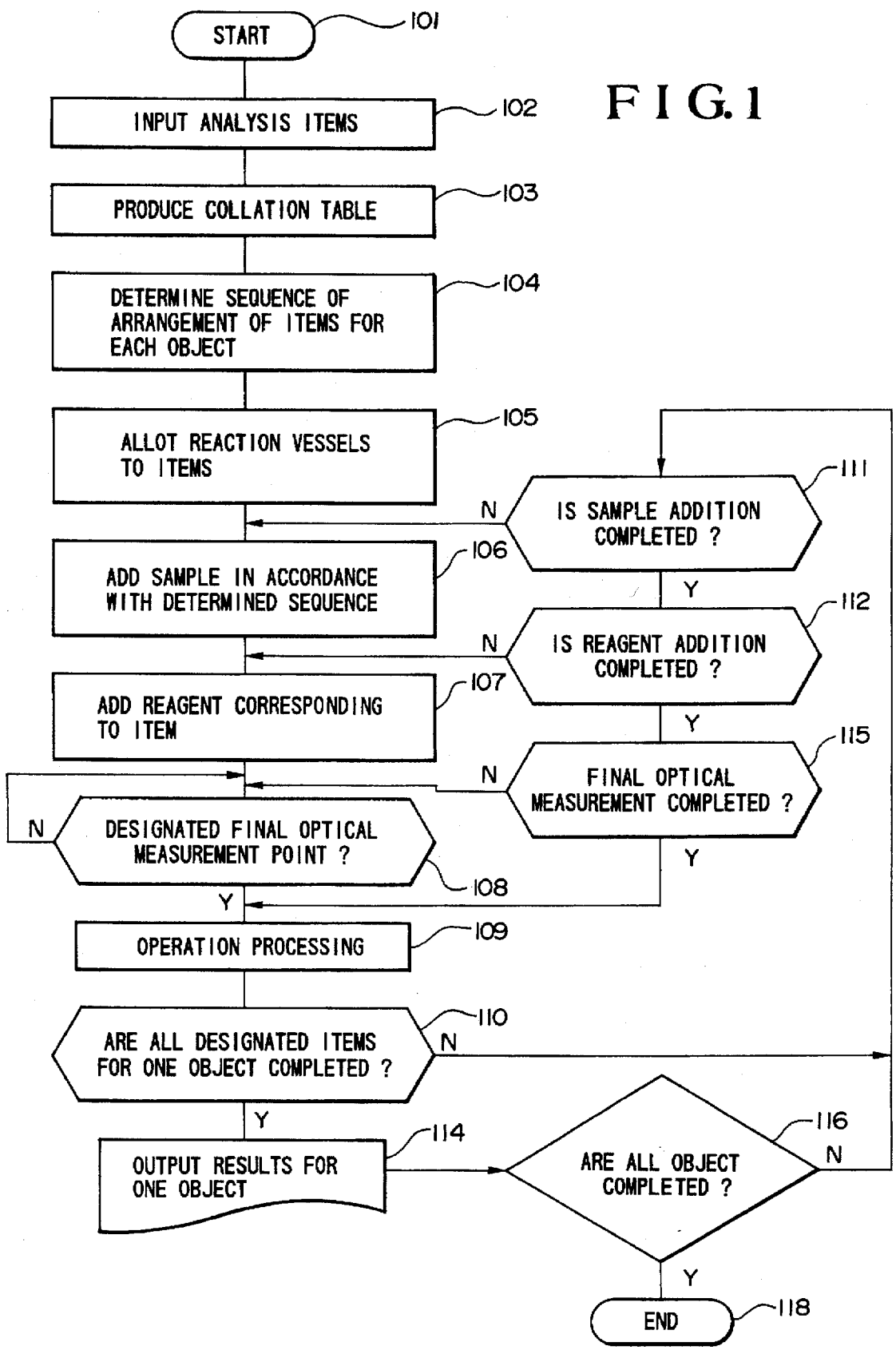
FIG. 1 is a flow chart for explaining the operation of an embodiment of the present invention.

FIG. 1 shows a flow chart of the routine operation of the analyzer shown in FIG. 3. In a usual case, measuring conditions concerning all possible analysis items capable of being measured by the analyzer shown in FIG. 3 are beforehand registered in the controller or microcomputer 15 by use of setting tables as shown in FIG. 2. Therefore, the operation for setting such measuring conditions is omitted from FIG. 1.

Referring to FIG. 1, when the analyzer adapts a stand-by condition (step 101), an operator designates or inputs analysis items for each of all objects or samples set on the sample disk 5 (step 102). Analysis request information inputted from the operation panel 25 is stored into the random access memory in the microcomputer 15. The analysis items are inputted in the order described in an inspection request irrespective of final optical measurement points of time, reaction times, etc.

When informed that the designation of the plurality of analysis items for each sample or, object included in the sample cups 35 has been completed, the microcomputer 15 produces a collation table concerning the analysis items requested for each object (step 103). For example, provided that seven analysis items as shown in Table 1 are designated for one object or sample, the microcomputer 15 compares the seven items in connection with a period of time from the start of a processing operation or the start of a reaction on the reaction line until the completion of the final optical measurement necessary for an operation for the determination of the value of density or activity to select an analysis item requiring substantially the longest time, and memorizes the selected analysis item so that it is arranged or registered at the first or top position of a collation table.

Next, in step 104, the microcomputer 15 performs an operation about the sequence in which the remaining analysis items other than the first analysis item should be arranged in the collation table. This operation is made to determine a sequence in which a time from the start of a processing operation for the analysis item group of the object under consideration until the completion of the final optical measurement for all the analysis items becomes the shortest. In a usual case, the sequencing is made from an item having a longer period of time until the final optical measurement point of time toward an item having a shorter period of time. After all the analysis items concerning one object have been registered in the collation table, the controller or microcomputer 15 as sequence determining means produces a collation table for the next object to be analyzed. Similarly, the sequence of arrangement of analysis items is determined for each of the remaining objects and is registered into the storage section of the controller. Thereby, the production of the collation tables for all the objects to be analyzed is completed.

The sequence of arrangement of analysis items in such a collation table corresponds to the sequence of supply or addition of aliquot portions of each sample. In the case where the analysis items shown in Table 1 are combined, the sequence of arrangement of those items results in A, E, F, B, D, C, G. This sequence is used as an operating condition of various parts including the allotment of reaction vessels on a reaction line, a sample supply or addition sequence, a reagent supply or addition sequence, and optical measurement processing.

Figure 5:
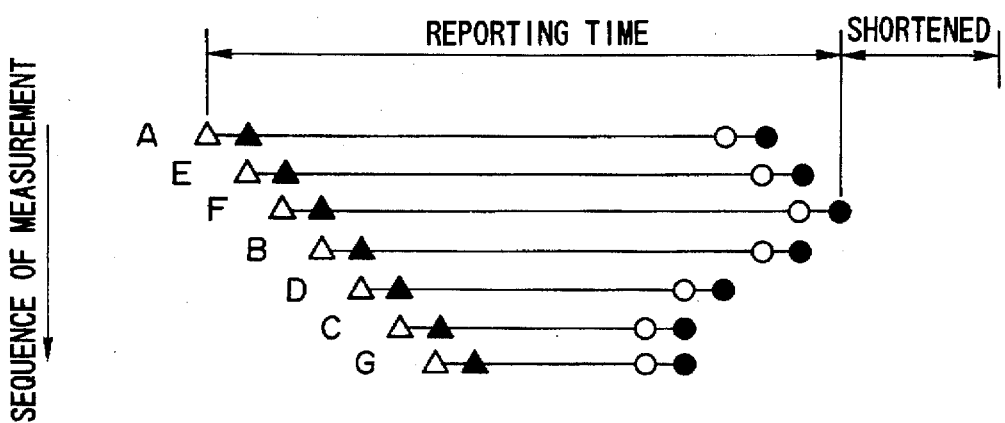
FIG. 5 is a diagram for explaining a processing time in the case where the present invention is applied.

In step 105, all the reaction vessels on the reaction are allotted to the analysis items for all the objects and this allotment is registered into the storage section. In the case of the object shown in Table 1, the allotment of the analysis items for reaction vessels in a reaction vessel group on the reaction line corresponding to that object is made such that the items are allotted successively from a reaction vessel at the top of that group in the sequence of A, E, F, B, D, C, G. Thereafter, the analyzer enters an operation for processing the object set on the sample disk 5. Though the analyzer shown in FIG. 5 is constructed such that a reagent is added after a sample has been added, the sequence of addition of a sample and a first reagent into the reaction vessel array may be reversed. A point of time when a sample or a reagent for the analysis of a certain object is first added into a reaction vessel is termed a point of time of the start of a processing operation for that object. A point of time when both the sample and the reagent are added into the reaction vessel is termed a point of time of the start of a reaction.

In step 106, the microcomputer 15 instructs the sample pipetter 21, the sample pipetting mechanism 7, the sample disk 5, the reaction disk 1, and so on to operate so that the volumes of sample necessary for the measurements about the analysis items are added or pipetted into the reaction vessels 2 in accordance with the previously determined sequence of arrangement of the analysis items. Thereby, the sample is added onto the reaction line upon each temporary stop. As for the object shown in Table 1, there is formed an array of reaction vessels in which the analysis items are arranged in the sequence of A, E, F, B, D, C, G.

When each of these reactions is temporarily stopped at the reagent adding position, a specified reagent corresponding to that reaction vessel is added (step 107). The number of reagents added is one at the smallest and four at the largest. Since the reaction disk 1 makes a rotating operation as mentioned earlier, optical measurement for all the reaction vessels is possible at every reagent addition.

In step 107, the reagent disks 9A and 9B are rotated through a control by the microcomputer 15 so that in accordance with the sequence of analysis items registered in the collection table, reagent reservoirs 40A and 40B containing reagents corresponding to the analysis items are located at the reagent suction positions 43 and 44. When reaction vessels allotted to those analysis items are temporarily stopped at the reagent adding positions 36 and 37 on the reaction disk 1, the reagents in the reagent reservoirs 40A and 40B corresponding to those analysis items are added into the reaction vessels by means of the reagent pipetting nozzles 41A and 41B.

In step 108, for each of all reaction vessels passed through the optical measurement point 33, the decision is made as to whether or not the final optical measurement point designated for the corresponding analysis item is reached. In the case where the final optical measurement point is not reached, the optical measurement operation is continued. The reaction solution of an analysis item, which reached the final optical measurement point, proceeds to succeeding step 109 for operation processing. Since optical measurement data necessary for an operation concerning each analysis item are stored in the floppy disk 24, the computer 15 uses those measurement data to perform an operation for determining the value of density or activity for the corresponding analysis item and stores the result in its own storage section.

In step 110, a point of time of the completion of data processings for all analysis items requested or designated for one object is monitored. As soon as the data processings for all analysis items are completed, the flow proceeds to step 114 in which the results of operation for one object are outputted.

In the case where optical measurement for all analysis items designated for one object is not completed in step 110, the flow proceeds to step 111. In step 111, the decision is made as to whether or not the sample addition is completed for the remaining analysis items. Also, in step 112, the decision is made as to whether or not the reagent addition is completed. Further, in step 115, the decision is made as to whether or not the final optical measurement is completed for the remaining analysis items.

In step 116, the decision is made as to whether or not the analysis processing is completed for all the objects requested. When not completed, the flow returns to step 111. When completed, the overall analysis operation is finished in step 118.

Figure 4:
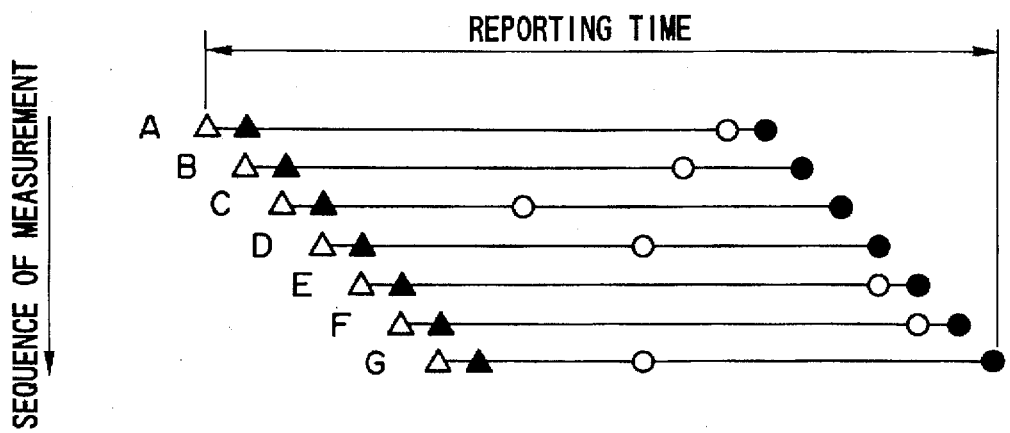
FIG. 4 is a diagram for explaining a processing time in the case where the present invention is not applied.

FIGS. 4 and 5 are diagrams for explaining the effect of the improvement in processing ability when the present invention is applied. FIGS. 4 and 5 show the cases where the present invention is not applied and is applied, respectively, in conjunction with the objects shown in Table 1.

When analysis concerning a plurality of analysis items is requested for one object, a time (T), after a processing for that object on a reaction line is started and until the overall data processing is completed and the results of measurement for the object are outputted together, is represented by $$T = T_m + n \times t \tag{1}$$

where $T_m$ is the uniformly or equally fixed data processing timing, n is the number of request items for the object and t is the machine cycle time for sample addition. The machine cycle in the analyzer shown in FIG. 3 corresponds to a time from the sample addition for the first item until the sample addition for the second item, for example 20 seconds.

In the case where the sample addition is made in the sequence of input of items designated for the object and the data processing is performed at equal intervals, as shown in FIG. 4, T amounts to 12 minutes and 20 seconds since $T_m=10$ minutes, n=7 and t=20 seconds.

On the other hand, in the case where the present invention is applied so that the sample supply or addition sequence or the sequence of arrangement of items is changed, as shown in FIG. 5, the completion of data processing for the item F (albumin) is the latest and hence T amounts to 11 minutes since $T_m=10$ minutes, n=3 and t=20 seconds. Accordingly, the processing time in the example shown in FIG. 5 is shortened by 1 minute and 20 seconds as compared with that shown in FIG. 4. namely, the processing ability is improved by 11%.

Seeing from an operator's standpoint the above-mentioned embodiment of the automatic analyzer capable of analytical measurement for a plurality of analysis items, when inputting measuring conditions into the automatic analyzer, the operator can set the conditions irrespective of the lengths of reaction times. Upon actual sample analysis, the designation of requested analysis items suffices for the operator and the analyzer determines automatically the sequence of sample supply for the analysis items and performs a sample supplying or analytical operation. Accordingly, the analytical operation can be performed efficiently with no troublesome operation.

We claim:

1. An analyzing method for a liquid sample in which a single sample to be analyzed about a plurality of analysis items is subjected to reactions in reaction vessels on a single reaction line and to optical measurement at a common optical measurement position, the method comprising the steps of:

indicating a final photometry point for an analysis item in a predetermined display column on a display from which an analysis condition is set for said analysis item;

(b) storing the final photometry point indicated by the indicating step;

(c) designating a group of analysis items for each of a plurality of samples;

(d) comparing processing times of the group of analysis items designated for a single sample, said processing times being reaction time intervals from a start of a reaction of the sample in a reaction vessel to the final photometry point;

determining a sequence for analyses of the group of analysis items designated for the single sample, wherein the sequence begins with the analysis item having the longest processing time, followed by successive analysis items with decreasing processing times, and ends with the analysis item having the shortest processing time;

selecting, from among the group of analysis items designated for said single sample, an analysis item for which the processing time is the longest of all said analysis items;

adding the sample into reaction vessels on a single reaction line with the reaction vessel corresponding to the selected analysis item being the first to which the sample is added;

successively adding aliquot portions of the single sample to the reaction vessels corresponding to the remaining analysis items in accordance with the sequence determine by said sequence determining step;

adding reagents corresponding to the analysis items into the reaction vessels allotted in accordance with the ordered sequence of the analysis items;

wherein reactions between the reagents and the aliquot portions occur in parallel on the single reaction line.

2. An analyzing method for a liquid sample according to claim 1, wherein the time between adding the sample into a reaction vessel on the single reaction line with a selected analysis item and the optional measurement of the selected analysis item differs among the plurality of analysis items.

3. An analyzing method for a liquid sample according to claim 1, wherein the selecting, adding and successively adding steps are performed for a plurality of samples, the ordered sequence being determined separately for each sample.

4. An analyzing apparatus for a liquid sample, including transporting means for intermittently transporting an array of reaction vessels on a single reaction line, sample supplying means for adding aliquot portions of a single sample into the reaction vessels on said single reaction line, and photometer means for optically measuring reaction solutions produced by mixtures of samples and reagents in the reaction vessels at a common fixed optical measurement position on said single reaction line, the apparatus comprising:

storage means for storing analysis items;

input means for sequentially inputting a plurality of analysis items for said single sample to the storage means, said analysis items including an analysis item of which a reaction time interval from a start of a reaction between the sample and a reagent until completion of effective final photometry of a reaction solution produced by the reaction is different from corresponding reaction time intervals of the other analysis items for the single sample;

sequence determining means for determining, for said single sample, a sequence of the analysis items to be analyzed so that, of all of the analysis items for the sample, the reaction vessel corresponding to the analysis item having the longest reaction time interval is first supplied followed by successive analysis item with decreasing reaction times, and the reaction vessel corresponding to the analysis item having the shortest reaction time interval is supplied last, the sequence of the reaction vessels being determined without regard to the input sequence of the inputted analysis items;

sample supplying means for adding aliquot portions of the single sample, in accordance with the analysis sequence determined by said sequence determining means, into reaction vessels which are allotted to the analysis items so that the analysis items are arranged on said single reaction line in accordance with said analysis sequence;

reagent supplying means for successively adding respective reagents corresponding to the analysis items in an order based on information from said sequence determining means, into the reaction vessels which are successively stopped at reagent adding positions on said single reaction line;

display means for displaying input columns for analysis item, optical measurement point, and operation timing on a display screen;

input means for inputting respective corresponding data into said input columns when said input columns are displayed;

control means for storing the data input by said input means into a storage section; and data storage means for storing data concerning the sequence of the analysis items determined by the sequence determining means for said single sample;

wherein reactions between the reagents and the aliquot portions occur in parallel on the single reaction line.

5. An analyzing method for a liquid sample in which a single sample to be analyzed about a plurality of analysis items is subjected to reactions in reaction vessels on a single reaction line and to optical measurement at a common photometry position, the method comprising the steps of:

indicating a final photometry point for an analysis item in a predetermined column on a display from which an analysis condition is set for said analysis item;

storing the final photometry point indicated by the indicating step;

designating a group of analysis items for each of a plurality of samples;

comparing processing times of the group of analysis items designated for a single sample, said processing times being reaction time intervals from a start of a reaction of the sample in a reaction vessel to the final photometry point;

determining a sequence for analyses of the group of analysis items for the single sample, wherein the sequence begins with the analysis item having the longest processing time followed by successive analysis items with decreasing processing times, and ends with the analysis item having the shortest processing time;

successively adding, in accordance with the sequence determined by said sequence determining step, aliquot portions of the single sample into reaction vessels allotted in correspondence to the analysis items on the single reaction line;

adding reagents corresponding to the analysis items into the reaction vessels in accordance with the sequence determined by said sequence determining step;

transferring the single reaction line of reaction vessels to pass the respective reaction vessels through the common photometry position plural times, for optical measurement of the analysis items; and determining one of density and enzyme activity for each analysis item upon completion of the optical measurement at the final photometry point.

6. An analysis method for a liquid sample according to claim 5, further comprising the steps of displaying input columns for analysis item name, optical measurement point and operation timing on a display screen capable of displaying parameters for analysis, while displaying data inputted from an input device in the corresponding input columns, and storing the data displayed in the input columns into a memory.

7. An analyzing method for a liquid sample according to claim 6, wherein said optical measurement point input column includes columns in which an application start optical measurement point and the final optical measurement point indicative of a time zone used for an operation for determining the value of activity for an analysis item for which a rate assay is to be made can be inputted.

8. An analyzing method for a liquid sample according to claim 5, wherein the inputting, determining and adding steps are performed for a plurality of samples, the sequence of analysis items to be delivered being determined separately for each sample.

9. An analyzing apparatus for a liquid sample, comprising:

a sample adding section for adding, on a single reaction line formed by an array of reaction vessels, aliquot portions of a single sample to be analyzed about a plurality of analysis items, into reaction vessels which are allotted to correspond to the analysis items;

a reagent adding section for adding a reagent corresponding to each analysis item into a reaction vessel on said single reaction line which corresponds to that analysis item;

optical measurement means for optically measuring plural times at a common optical measurement position each reaction vessel on said single reaction line which contains an aliquot portion of the single sample and a reagent;

sequence determining means for determining the sequence of analysis for said analysis items based on time required for processing each analysis item from a start of a reaction until completion of optical measurement, and without regard to the input sequence of analysis items, wherein the sequence begins with the analysis item having the longest processing time followed by successive analysis items decreasing processing times, and ends with the analysis item having the shortest processing time;

means for operating said sample adding section and said reagent adding section on the basis of information from said sequence determining means so that the sample and the reagent are added into reaction vessels in accordance with the sequence determined by said sequence determining means, and so that reactions between the reagents and the aliquot portion occur in parallel on the single reaction line;

input means for inputting a specified one of a plurality of optical measurement points settable in accordance with the distance of movement of a reaction vessel with a correspondence to an analysis item; and display means for displaying an optical measurement point of time designated corresponding to an analysis item with a correspondence to that analysis item.

10. An analyzing apparatus for a liquid sample according to claim 9, further comprising means for causing the photometer means to optically measure each of the reaction solutions after a respective predetermined time following the addition of the sample into a reaction vessel to an analysis item, wherein the respective predetermined times differ among the plurality of analysis items.

* * * * *